| United States Patent [19] | [11] Patent Number: 4,670,561 |
| Blum et al. | [45] Date of Patent: Jun. 2, 1987 |

[54] PROCESS FOR OBTAINING HYDROCHLORIC SALTS OF 2, 5, 6-TRIAMINO-4 (1H)-PYRIMIDINONE

[76] Inventors: Holger Blum, Parkallee 75, D-2000 Hamburg 13; Gernot Dreesmann, Vogt-Groth-Weg 69, D-2000 Hamburg 52, both of Fed. Rep. of Germany

[21] Appl. No.: 789,310

[22] PCT Filed: Jan. 2, 1985

[86] PCT No.: PCT/EP85/00001
§ 371 Date: Nov. 14, 1985
§ 102(e) Date: Nov. 14, 1985

[87] PCT Pub. No.: WO85/03506
PCT Pub. Date: Aug. 15, 1985

[30] Foreign Application Priority Data

Feb. 1, 1984 [DE] Fed. Rep. of Germany ....... 3403468

[51] Int. Cl.$^4$ .................. C07D 239/22; C07D 239/50
[52] U.S. Cl. .................................................. 544/320
[58] Field of Search ........................................ 544/320

[56] References Cited

FOREIGN PATENT DOCUMENTS 955539 1/1950 France .
49065 3/1965 Poland .

OTHER PUBLICATIONS

Storm, et al.; J. of Org. Chem., 36, (1971), pp. 3925–3927.
"Journal of Heterocyclic Chem.", 9 (1972), pp. 481–487, Young–Ho Kim et al.
"Bull. Soc. Chim.", 1946, pp. 80–85, Polonovski et al.

Primary Examiner—Joseph Paul Brust
Attorney, Agent, or Firm—Birch, Stewart Kolasch & Birch

[57] ABSTRACT

A process for preparing hydrochloric salts of 2,5,6-triamino-4(1H)-pyrimidinone (TAP) with a low content of organic foreign substances which comprises reacting the reduction product of 2,6-diamino-5-nitroso-4(1H)-pyrimidone (DNAP) with hydrogen chloride, wherein the reaction medium comprises water, hydrogen chloride and isopropyl alcohol.

7 Claims, No Drawings

PROCESS FOR OBTAINING HYDROCHLORIC SALTS OF 2, 5, 6-TRIAMINO-4 (1H)-PYRIMIDINONE

The invention relates to a process for obtaining the hydrochloric salt of 2,5,6-triamino-4(1H)-pyrimidinone (TAP) with a low content of organic foreign substances by reacting the reduction product of 2,6-diamino-5-nitroso-4(1H)-pyrimidinone (DANP) with hydrogen chloride. The TAP has the Chemical Abstracts Register Number 51 324-37-9, the DANP has got the Chemical Abstracts Register Number 2 387-48-6.

The reduction of DANP which leads to the free TAP base is carried out technically in an aqueous alkaline solution at 40° to 80° C. either
  (a) by reduction with sodium sulfide according to Polish Patent document No. 49065. The free TAP base being hot is filtered off from the deposited sulfur, and a reaction product consisting substantially of free TAP base and TAP dihydrogen chloride, is separated by salting out with ammonium chloride at a pH of 2; or
  (b) by reaction with hydrogen in natron alkaline solution with Raney nickel or noble metals as catalyst according to French Patent document No. FP 955539. The TAP as a slightly soluble reaction product in form of a sulfate, resulting from acidifying the solution to a pH of 2 with sulfuric acid, is deposited in the diluted solution from which the Raney nickel has been filtered off.

Both processes provide reaction products which still contain five to ten mole percent, based on the amount of TAP being present, of foreign organic accompanying substances:
non-reacted DANP (insoluble in water below pH 8),
deamination products of DANP,
deamination products of TAP,
intensively colored polynuclear autoxidation products of TAP.

For chemical reactions in an aqueous/alcoholic solution the TAP has to be present in the form of a readily soluble dihydrogen chloride (C. B. Storm, J. org. Chem. 36 (1971), 3925).

According to (a) (Polish Patent document No. 49065) the TAP-di-HCl could be separated from the reaction product by dissolving said reaction product in aqueous hydrochloric acid, and which would also dissolve the foreign organic accompanying substances.

According to Y. Kim, Journal of Heterocyclic Chem. 9 (1972), page 485, TAP-di-HCl can be obtained by reacting TAP sulfate with aqueous barium chloride solution, wherein the solution formed also contains an excess of barium ions in addition to the foreign organic accompanying substances, which renders the solution dangerous from a physiological standpoint.

In chemical reactions of the TAP solutions obtained according in the aforementioned manner, the foreign organic accompanying substances mostly react with the reagents introduced, and thus the endproducts produced, are difficult to purify.

The products prepared from TAP are mostly natural substances or important pharmaceutical components, such as Guanine, Xanthine, Folic acid and Biopterin. This class of compounds, purines and pteridines, are chemically unstable and may be subjected to partial fragmentation by the application of the necessary purifying procedures, whereby a further impurity and in any case a loss of yield would be expected.

Attempts have already been made to remove the foreign organic accompanying substances from the reduction product of DANP by repeatedly recrystallizing the TAP sulfate from hot 2% sulfuric acid with the aid of activated carbon (Polonovsky et.al. Bull. Soc. Chim. 1946, 80 to 85). Although this method finally achieves the goal intended, said method is complicated and expensive, since TAP sulfate hardly dissolves even in hot 2% sulfuric acid, and to work with large volumes, is unavoidable. Additionally, in a second reaction step, the TAP sulfate so purified still has to be reacted with $BaCl_2$ to obtain TAP-di-HCl.

Accordingly, the object of the invention is to prepare TAP-di-HCl of the formula (i.e. the tautomeric hydroxy form thereof):

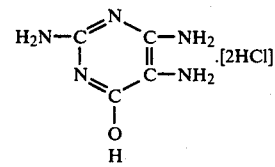

with small amounts (i.e. less than 1 mole percent) of foreign organic substances in a technically simple and economic manner, directly from the reduction products of DANP with a single purification process.

It was now found that this problem can be solved by reacting a reduction product of DANP, obtained according to the aforementioned processes (a) or (b), in a reaction medium of hydrogen chloride, water and isopropyl alcohol. The temperature of the reaction medium is between about 60° and 120° C., and the treatment period is between 24 hours at 60° C. and ten minutes at 120° C.

It was found that a remarkable portion of the organic impurities accompanying the TAP, can be removed by reacting with hot hydrochloric acid alone. In a single step reaction, however, after the addition of isopropyl alcohol with about 20 weight percent in the reaction medium only, contents of foreign substances being lower than 1 mole percent can be achieved.

According to the invention, it is also possible to carry out the purifying procedure in a single step with two phases in such a manner that a portion of the foreign substances is first removed with hot hydrochloric acid, and then the remaining organic foreign substances are separated by the addition of isopropyl alcohol.

The temperature can be the same in each phase of the purification. However, the treatment with hydrochloric acid can also be carried out at temperatures between 80° and 120° C.

A particular advantage of the process according to the invention is the fact that it makes possible the direct deposition of pure TAP-di-HCl from the filtered reduction solution of the Raney-nickel-hydrogenation. Accordingly, the filtered alkaline reduction solution is acidified to a pH of 2 and concentrated, without effecting the intermediate step of deposition of TAP-sulfate with $H_2SO_4$, which intermediate step is affected with losses of yield. The sirup-like paste of crystals is then subjected to the purifying procedure according to the invention, whereby pure TAP-di-HCl is obtained with a yield of about 90 percent, based on DANP.

EXAMPLE 1

Various reaction media have been prepared by introducing hydrogen chloride gas into water/alcohol mixtures. The composition of the reaction media with respect to the alcohol and the hydrochloric acid can be taken from the following table, wherein in each case the portion of water corresponds to the remaining percentage up to 100 weight percent. In the reaction media so prepared, there was suspended the crude reduction product of DANP in form of the impure TAP sulfate or the TAP-mono-HCl. The suspensions contained about 0.2 to 0.25 mole TAP salt per kilogram reaction medium. As indicated in the table, the mixtures optionally have been kept under a weak excess pressure during the period of the mentioned time at about 80° C., subsequently cooled below 30° C., and the crystals of TAP-di-HCl have been washed with isopropyl alcohol. After drying under vacuum at 40° C. the crystals have been analyzed.

The analysis was made iodometrically according to the method as reported by M. Z. Grynberg, Biochemische Zeitschrift, Vol. 253 (1932), p. 143 to 145. According to said method, 1 mole TAP-salt consumes 4 gram atoms iodine. Impurities can be noted by a consumption of more or less iodine. Contrary to this, the elementary analytical determination method based on C,H,N, which method is also indicated, can be used within a certain limit, only because apparently impurities are not distinguished.

TABLE

| No. | starting compound | w. % HCl | w. % alcohol | reaction time | temperature | purity (C,H,N) | purity iodometrical |
|---|---|---|---|---|---|---|---|
| 1 | TAP sulfate | 20 | — | 1 hour | 80° C. | 95 mole % | 93 mole % |
| 2 | TAP sulfate | 15 | 30 methanol | 1 hour | 80° C. | 95 mole % | 93 mole % |
| 3 | TAP sulfate | 15 | 30 ethanol | 1 hour | 80° C. | 98.4 mole % | 94 mole % |
| 4 | TAP sulfate | 15 | 30 isopropanol | 1 hour | 80° C. | 99.3 mole % | 99.6 mole % |
| 5 | TAP mono-HCl | 20 | 40 isopropanol | 1 hour | 80° C. | 99.2 mole % | 99.6 mole % |
| 6 | TAP sulfate | 10 | 20 isopropanol | 1 hour | 80° C. | 99 mole % | 98.5 mole % |
| 7 | TAP sulfate | 15 | 50 isopropanol | 1 hour | 80° C. | 99.2 mole % | 100.2 mole % |

Note:
The crude TAP sulfate used had a purity of 92 weight percent by elementary analysis and a purity of 103 mole percent by iodometry.
The crude TAP-mono-HCl had a purity of 89 mole percent by elementary analysis and a purity of 94 mole percent by iodometry.

EXAMPLE 2

18 gram of the crude TAP sulfate as used in example 1 have been suspended in 310 gram 20% hydrochloric acid. The mixture was heated to 100° C., whereby a solution was obtained. After 20 min the solution was cooled to 80° C., and 200 gram isopropyl alcohol have been added. Than it was stirred still 60 min at 80° C.

The yellowish reaction solution was cooled to 25° C., and the white crystals of TAP-di-HCl have been filtered off and washed with a small amount of isopropyl alcohol. Yield 12.2 gram with a iodometric purity of 99.7 mole percent.

We claim:

1. A process for obtaining a dihydrochloride salt of 2,5,6-triamino-4(1H)-pyrimidinone of the formula (in the tautomeric hydroxy form thereof):

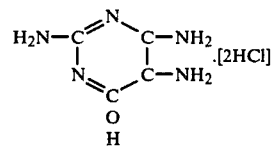

with a content of organic foreign substances of less than 1 mole percent, which comprises reacting a reduction product of 2,6-diamino-5-nitroso-4(1H)-pyrimidinone with hydrogen chloride, at a temperature of about 60°–120° C. and in a reaction medium consisting essentially of water, hydrogen chloride and at least 20 weight percent isopropyl alcohol with the proviso that the isopropyl alcohol need not be present at the start of the reaction, wherein said reduction product is obtained by the reduction of 2,6-diamino-5-nitroso-4(1H)-pyrimidinone with sodium sulfide in an aqueous alkaline solution or with hydrogen in a natron alkaline solution which further comprises Raney nickel or a noble metal as catalysts, at 40° to 80° C.

2. A process according to claim 1, wherein the reaction medium contains at least 10 weight percent of hydrogen chloride.

3. A process according to claim 1, in which said reaction medium consists essentially of water, hydrogen chloride and isopropyl alcohol at the start of the reaction.

4. A process according to claim 1, in which said reaction medium consists essentially of water and hydrogen chloride at the start of the reaction and isopropyl alcohol is subsequently added.

5. A process according to claim 3, wherein the reaction medium contains at least 10 weight percent of hydrogen chloride.

6. A process according to claim 4, wherein the reaction medium contains at least 10 weight percent of hydrogen chloride.

7. A process according to claim 1, wherein the reaction period is between 24 hours and 10 minutes.

* * * * *